(12) United States Patent
Sullivan et al.

(10) Patent No.: US 9,568,459 B2
(45) Date of Patent: Feb. 14, 2017

(54) METHOD AND SYSTEM FOR DETERMINING ASPHALTENE ONSET PRESSURE USING A USING DEPRESSURIZATION AND PRESSURIZATION

(71) Applicant: SCHLUMBERGER TECHNOLOGY CORPORATION, Sugar Land, TX (US)

(72) Inventors: Matthew T. Sullivan, Westwood, MA (US); Christopher Harrison, Auburndale, MA (US); Shunsuke Fukagawa, Arlington, MA (US); Elizabeth Smythe, Cambridge, MA (US); John Meier, Boston, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 9 days.

(21) Appl. No.: 14/262,480

(22) Filed: Apr. 25, 2014

(65) Prior Publication Data
US 2015/0309003 A1 Oct. 29, 2015

(51) Int. Cl.
*G01N 33/28* (2006.01)
*E21B 47/06* (2012.01)
(Continued)

(52) U.S. Cl.
CPC .......... *G01N 33/2835* (2013.01); *E21B 47/06* (2013.01); *G01N 21/3577* (2013.01);
(Continued)

(58) Field of Classification Search
CPC ................ E21B 47/102; E21B 49/08–49/10; G01N 33/2823; G01N 33/2835; G01N 33/28–33/30;G01N 21/8507; G01N 2021/855
See application file for complete search history.

(56) References Cited

U.S. PATENT DOCUMENTS 5,691,809 A * 11/1997 Tackett .................. G01N 21/64
356/72
6,501,072 B2 * 12/2002 Mullins ................ E21B 47/102
250/255

(Continued)

FOREIGN PATENT DOCUMENTS

WO 0120322 A1 3/2001

OTHER PUBLICATIONS

Franco, Juliana C., et al. "Towards in situ fluorescence spectroscopy and microscopy investigations of asphaltene precipitation kinetics." Optics express 21.25 (2013): 30874-30885.*

(Continued)

*Primary Examiner* — Kara E Geisel
*Assistant Examiner* — Rufus Phillips
(74) *Attorney, Agent, or Firm* — Trevor G. Grove

(57) ABSTRACT

Methods and systems for determining for determining asphaltene onset pressure of a formation fluid are described herein. The method includes the following processes: (a) transmitting light through a sample of the formation fluid; (b) decreasing pressure of the sample; (c) detecting intensity of the transmitted light during depressurization; (d) identifying a change in intensity of the transmitted light during depressurization; (e) increasing pressure of the sample to a fixed pressure; and (f) detecting intensity of the transmitted light at the fixed pressure and at an equilibrated light intensity. Processes (a) to (f) are repeated for a number of different fixed pressures. The asphaltene onset pressure of the formation fluid sample can be determined using (i) the intensity of the transmitted light during each depressuriza- (Continued)

tion and (ii) the intensity of the transmitted light at each of the different fixed pressures.

19 Claims, 10 Drawing Sheets

(51) Int. Cl.
  *G01V 8/00* (2006.01)
  *G01N 21/3577* (2014.01)
  *G01N 21/59* (2006.01)
(52) U.S. Cl.
  CPC .............. *G01N 21/59* (2013.01); *G01V 8/00* (2013.01); *G01N 2201/08* (2013.01)

(56) References Cited

U.S. PATENT DOCUMENTS

| | | | |
|---|---|---|---|
| 7,196,786 B2 | 3/2007 | DiFoggio | |
| 8,028,561 B2 * | 10/2011 | Herz | G01N 33/2841 73/19.12 |
| 8,136,394 B2 | 3/2012 | Hsu et al. | |
| 8,335,650 B2 | 12/2012 | Hsu et al. | |
| 8,915,014 B1 | 12/2014 | Daugherty | |
| 2002/0139929 A1 | 10/2002 | Mullins et al. | |
| 2014/0268516 A1 | 9/2014 | Fathollahi et al. | |
| 2015/0309002 A1 | 10/2015 | Fukagawa et al. | |
| 2016/0040533 A1 | 2/2016 | Harrison et al. | |

OTHER PUBLICATIONS

International Search report in PCT/US2015/027476 filed Apr. 24, 2015 Jul. 31, 2015. 3 pages.
Written Opinion in PCT/US2015/027476 filed Apr. 24, 2015 Jul. 31, 2015. 12 pages.

* cited by examiner

METHOD AND SYSTEM FOR DETERMINING ASPHALTENE ONSET PRESSURE USING A USING DEPRESSURIZATION AND PRESSURIZATION

RELATED APPLICATION

The present application is related to U.S. application Ser. No. 14/262,462, filed on Apr. 25, 2014 and entitled "METHOD AND SYSTEM FOR DETERMINING ASPHALTENE ONSET PRESSURE USING A WAVELENGTH DEPENDENT SIGNAL."

TECHNICAL FIELD

This disclosure relates to fluid analysis, and more particularly to determining asphaltene onset pressure of a fluid.

BACKGROUND

Some formation fluids, such as oils, contain a substantial amount of asphaltenes. Asphaltenes are large molecules that are dissolved within formation fluids at high pressures. As the pressure of the formation fluid is reduced, the solubility of the asphaltenes within the fluid is also reduced and the asphaltenes will begin to flocculate. The pressure at which the asphaltenes begin to flocculate is known as asphaltene onset pressure (AOP). FIG. 1 shows the process of flocculation. As shown in FIG. 1, individual molecules of asphaltenes form nanoaggregates and then form clusters of nanoaggregates.

In the oil and gas industry, the asphaltene onset pressure of a formation fluid within a hydrocarbon reservoir formation is valuable information that is used for completing and producing a well. For example, during production of a well, the formation fluid that is extracted from the hydrocarbon reservoir is maintained above the known asphaltene onset pressure to avoid creation of asphaltene clusters within the formation. A build-up of asphaltenes within the formation can curtail production of the well.

Using one technique, asphaltene onset pressure is measured in a laboratory environment by measuring light transmission through a large formation fluid sample (e.g., 10 mL-100 mL). The light transmission is measured while slowly reducing the pressure of the sample (e.g., 100 psi/hour). The sample is agitated using a mixer to maintain equilibrium within the formation fluid and to avoid asphaltene flocculation from settling within the cell. As the pressure within the formation fluid sample is decreased, at a certain pressure, the light transmission will decrease significantly. The pressure and temperature at which the light transmission will decrease significantly is the asphaltene onset pressure and the asphaltene onset temperature. FIG. 2 shows how flocculation of asphaltenes reduces light transmission. As the enclosed volume is increased, the pressure of the oil sample decreases and asphaltenes begin to flocculate at the asphaltene onset pressure. At this point, the formation fluid sample turns opaque and reduces the transmission of light. An intense light source, such as a laser is used for such light transmission measurements. Another laboratory technique also uses a slow depressurization technique, but identifies asphaltene flocculation using microscopic observation. In yet another laboratory technique, the light transmission technique and the microscopic observation technique are combined so that light transmission and direct observation of flocculation are performed simultaneously.

While these slow depressurization techniques can be used in a laboratory environment, the techniques are not well suited for measurement of asphaltene onset pressure in a wellbore environment because the techniques use (i) a large formation fluid sample, (ii) additional mixing equipment, (iii) a large timescale for depressurization, and (iv) a bright light source, such as a laser.

Another factor that complicates measurement of asphaltene onset pressure is that asphaltene onset pressure can be confused with bubble point pressure. The bubble point pressure is the pressure at which at least a portion of a liquid changes phase to a vapor state (e.g., nucleates bubbles) at equilibrium. FIG. 3 shows a formation fluid sample in a liquid state within an enclosed volume. As the size of the enclosed volume is increased, the pressure of the formation fluid sample decreases and bubbles begin to form at the bubble point pressure. This formation of bubbles will also reduce the light transmission of a formation fluid sample. The decrease in light transmission occurs because bubbles form at the bubble point and the bubbles scatter light, which reduces light transmission. Accordingly, asphaltene onset pressure can be confused with bubble point pressure because both the asphaltene onset pressure and the bubble point pressure reduce transmission of light.

SUMMARY

Illustrative embodiments of the present disclosure are directed to a method for determining asphaltene onset pressure of a formation fluid. The method includes the following processes: (a) transmitting light through a sample of the formation fluid; (b) decreasing pressure of the sample; (c) detecting intensity of the transmitted light during depressurization; (d) identifying a change in intensity of the transmitted light during depressurization; (e) increasing pressure of the sample to a fixed pressure; (f) detecting intensity of the transmitted light at the fixed pressure and at an equilibrated light intensity; (g) repeating processes (a) to (f) for a number of different fixed pressures; and (h) determining asphaltene onset pressure of the sample using (i) the intensity of the transmitted light during each depressurization and (ii) the intensity of the transmitted light at each of the different fixed pressures.

Various embodiments of the present disclosure are also directed to a system for determining asphaltene onset pressure of a formation fluid. The system includes a source for generating light that is transmitted through a sample of the formation fluid and a detector for detecting light transmitted through the sample. The system further includes a pressure control unit that varies pressure of the sample and a controller that determines the asphaltene onset pressure of the formation fluid using (i) intensity of the transmitted light detected during each depressurization of the sample and (ii) intensity of the transmitted light at a number of different fixed pressures.

Further embodiments of the present disclosure are directed to another method for determining asphaltene onset pressure of a formation fluid. The method includes the following processes: (a) transmitting light through a sample of the formation fluid; (b) decreasing pressure of the sample; (c) detecting intensity of the transmitted light during depressurization; (d) identifying a change in intensity of the transmitted light during depressurization; (e) increasing pressure of the sample to a fixed pressure; (f) detecting intensity of the transmitted light at the fixed pressure; (g) repeating processes (e) to (f) for a number of different fixed pressures; and (h) determining the asphaltene onset pressure of the fluid sample using (i) the intensity of the transmitted light during depressurization and (ii) the intensity of the transmitted light at each of the different fixed pressures.

Various embodiments of the present disclosure are also directed to method for detecting asphaltene onset of a formation fluid. The method includes the following processes: (a) transmitting light through a sample of the formation fluid; (b) detecting intensity of the transmitted light while decreasing pressure of the sample; (c) detecting intensity of the transmitted light while increasing pressure of the sample; and (d) detecting asphaltene onset within the sample by identifying a difference in intensity between transmitted light during process (b) and transmitted light during process (c).

BRIEF DESCRIPTION OF THE DRAWINGS

Those skilled in the art should more fully appreciate advantages of various embodiments of the present disclosure from the following "Description of Illustrative Embodiments," discussed with reference to the drawings summarized immediately below.

DESCRIPTION OF ILLUSTRATIVE EMBODIMENTS

Illustrative embodiments of the disclosure are directed to a method and system for determining asphaltene onset pressure of a fluid sample, such as a formation fluid. The method includes the following processes: (a) transmitting light through a sample of the formation fluid; (b) decreasing pressure of the formation fluid sample; (c) detecting intensity of the transmitted light during depressurization; (d) identifying a change in intensity of the transmitted light during depressurization; (e) increasing pressure of the formation fluid sample to a fixed pressure; and (f) detecting intensity of the transmitted light at the fixed pressure and at an equilibrated light intensity. Processes (a) to (f) are repeated for a number of different fixed pressures. The asphaltene onset pressure of the formation fluid sample can be determined using (i) the intensity of the transmitted light during each depressurization and (ii) the intensity of the transmitted light at each of the different fixed pressure. In illustrative embodiments, this method efficiently determines asphaltene onset pressure by using smaller sample volumes and a shorter time scale, as compared to the laboratory techniques described above. Details of various embodiments are discussed below.

Figure 4:
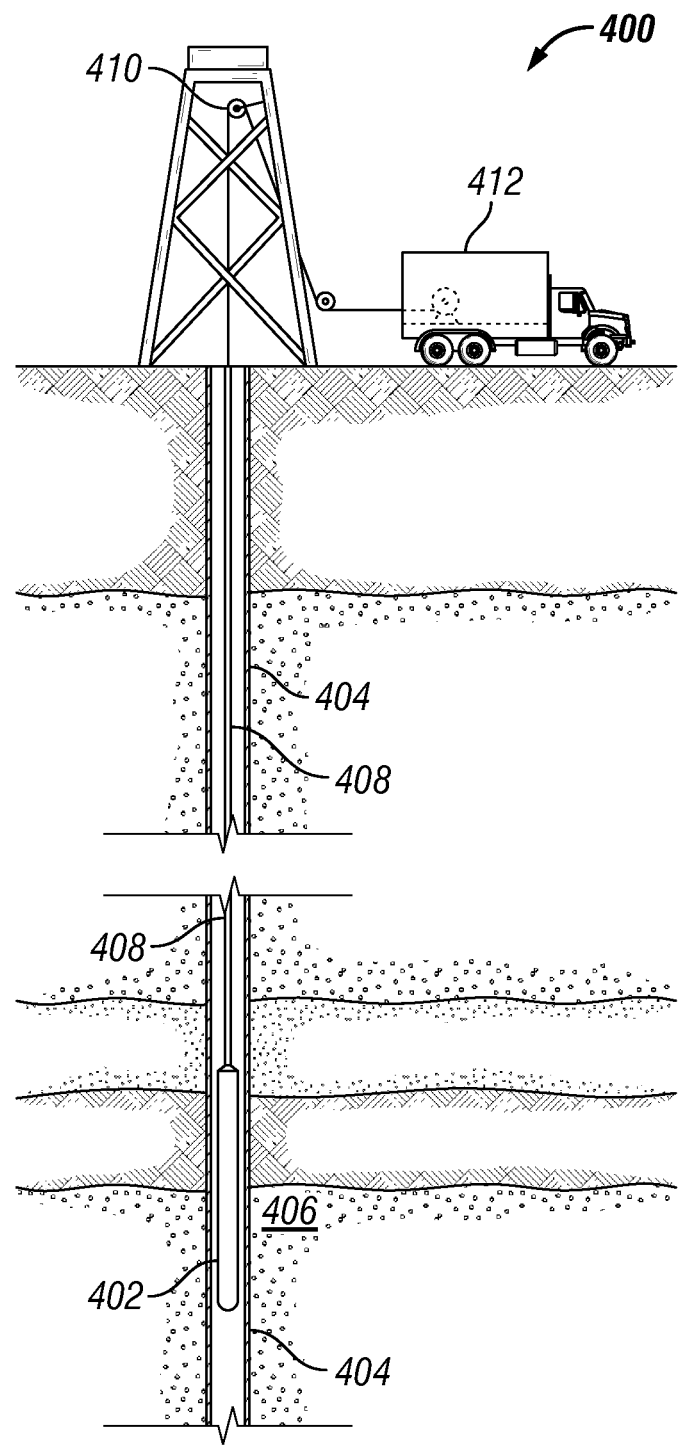
FIG. 4 shows a wireline logging system at a well site in accordance with one embodiment of the present disclosure.

FIG. 4 shows one example of a wireline logging system 400 at a well site. The wireline logging system 400 can be used to implement measurements of asphaltene onset pressure, as described herein. In this example, a wireline tool 402 is lowered into a wellbore 404 that traverses a formation 406 using a cable 408 and a winch 410. The wireline tool 402 is lowered down into the wellbore 404 and makes a number of measurements of the adjacent formation 406 at a plurality of sampling locations along the wellbore 404. The data from these measurements is communicated through the cable 408 to surface equipment 412, which may include a computer system for storing and processing the data obtained by the wireline tool 402. In this case, the surface equipment 412 includes a truck that supports the wireline tool 402. In another embodiment, however, the surface equipment may be located within a cabin on an off-shore platform.

Figure 5:
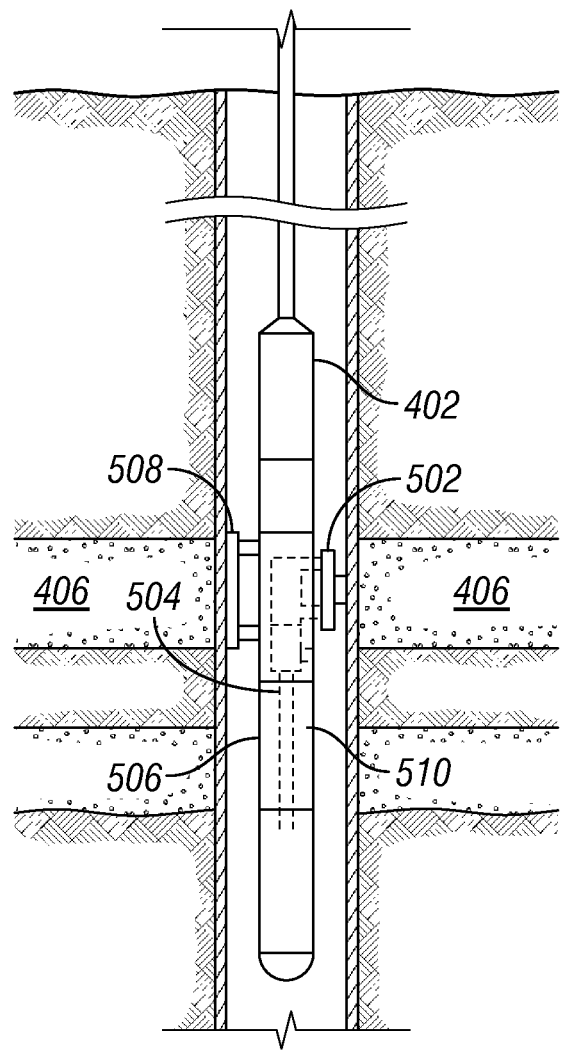
FIG. 5 shows a wireline tool in accordance with one embodiment of the present disclosure.

FIG. 5 shows a more detailed view of the wireline tool 402. The wireline tool includes 402 a selectively extendable fluid admitting assembly (e.g., probe) 502. This assembly 502 extends into the formation 406 and withdraws formation fluid from the formation 406 (e.g., samples the formation) and into the wireline tool 402. The formation fluid flows through the assembly 502 and into a flow line 504 within a housing 506 of the tool 402. A pump (not shown) can be used to withdraw the formation fluid from the formation 406 and pass the fluid through the flow line 504. The wireline tool 402 may also include a selectively extendable anchoring member 508 that is arranged to press the probe 502 assembly against the formation 406. The wireline tool 402 also includes a fluid analyzer module 510 for analyzing at least a portion of the fluid in the flow line 504. The fluid analyzer module 510 includes a system for determining asphaltene onset pressure of a fluid sample.

Figure 6:
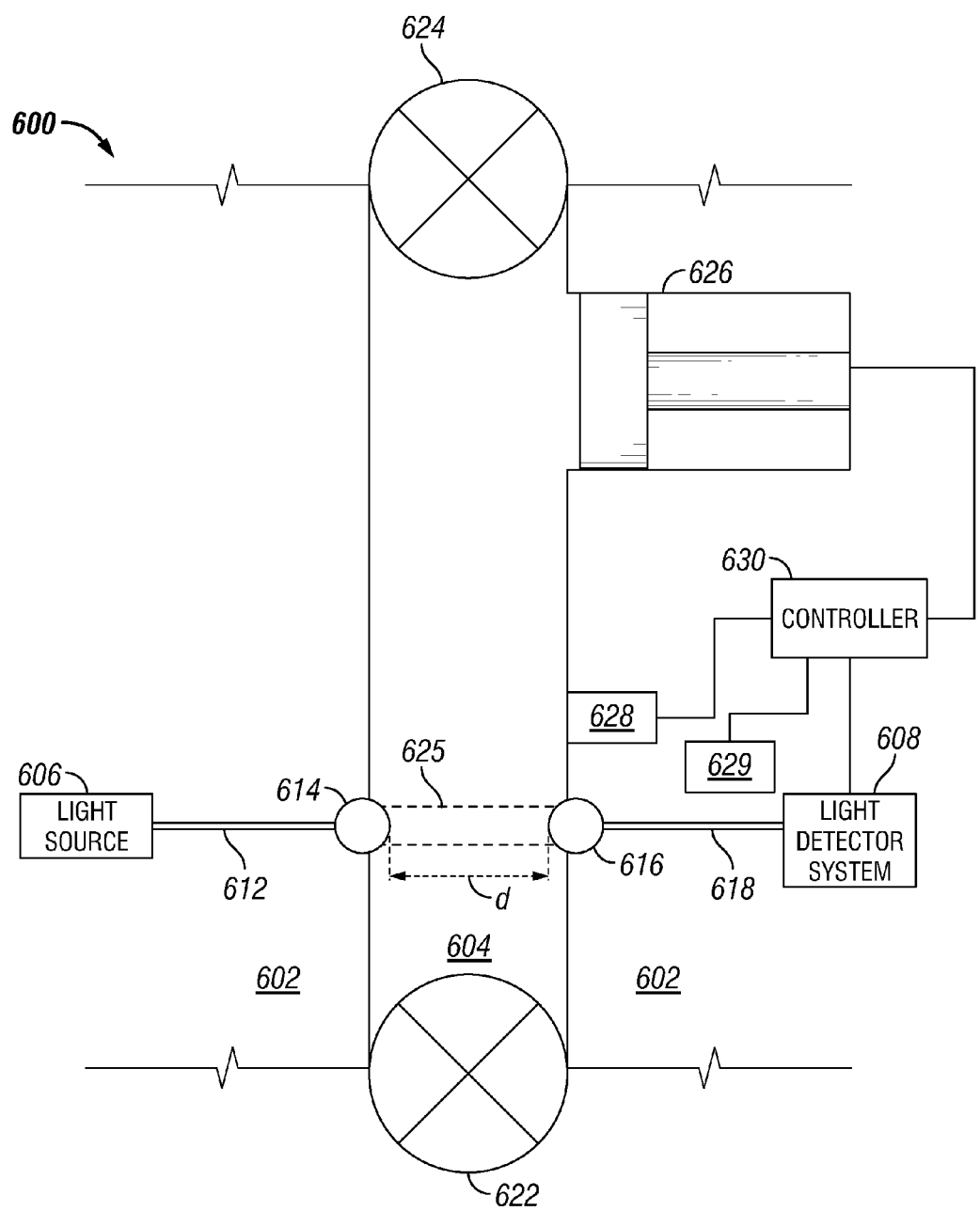
FIG. 6 shows a system for determining asphaltene onset pressure of a fluid sample in accordance with one embodiment of the present disclosure.

FIG. 6 shows a more detailed view of a system 600 for determining asphaltene onset pressure of a fluid sample. The system 600 includes a housing 602 that defines a detection chamber 604 for at least partially containing the fluid sample. In various embodiments, the housing 602 is formed from a metal material, such as steel or aluminum. In some embodiments, the detection chamber 604 is a channel that receives a fluid sample that is extracted from the flow line 504 of the wireline tool 402. In yet further embodiments, the channel may be a microfluidic channel that has a smallest diameter of less than 1 mm.

The system 600 also includes a light source 606 for generating light that passes through the fluid sample and a light detector system 608 for detecting transmitted light. The light can be of a variety of different wavelengths and can include visible light, ultraviolet light, and/or infrared light (e.g., near infrared light or mid-infrared light). In the specific embodiment shown in FIG. 6, the light source 606 is a tungsten halogen lamp that generates light and provides the light to a first optical fiber 612. A first ball lens 614 serves as both a window preventing outflow of the fluid sample and a lens that collimates the light from the optical fiber 612 into the detection chamber 604. The system 600 also includes a second ball lens 616 that serves as both a window preventing outflow and a lens that focuses the light signal from the detection chamber onto a second optical fiber 618. The second optical fiber 618 provides the transmitted light to the light detector system 608 (e.g., that includes one or more photodiodes). The light detector system 608 translates the transmitted light into a transmitted light signal that is representative of the intensity of the transmitted light.

Figure 7:
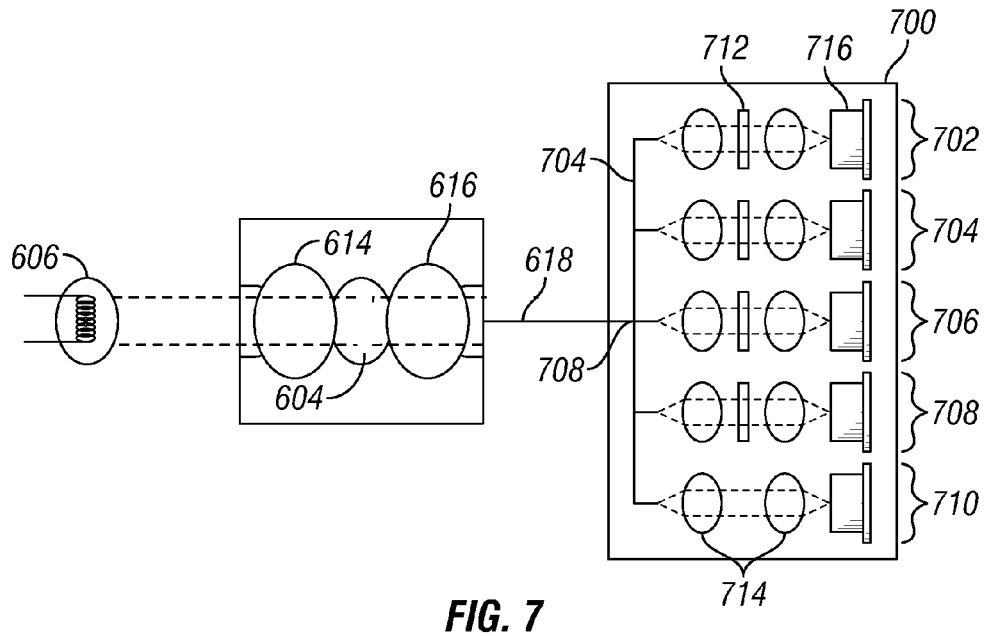
FIG. 7 shows a light detection system in accordance with one embodiment of the present disclosure.

FIG. 7 shows a light detector system 700 in accordance with one embodiment of the present disclosure. As shown in FIG. 7, a light source 606 generates light that passes through a first ball lens 614 and into a fluid sample. A second ball lens 616 focuses the light signal from the detection chamber 604 onto a second optical fiber 618. A splitter 702 splits light from the second optical fiber 618 and passes the light to a set of optical fibers 704. The set of optical fibers 704 provide the light from the splitter 702 to a number of detector modules. In this example, the light detector system 700 includes four wavelength-specific detector modules 702, 704, 706, and 708 for detecting light at a number of different specific wavelengths (e.g., the wavelength-specific detector modules are set to four specific spectroscopic channels). The light detector system 700 also includes a broadband detector module 710 that detects intensity of light over a wide range of wavelengths and is used to determine whether a phase change has occurred within the fluid sample (e.g., asphaltene onset or bubble point). The wavelength-specific detector modules 702, 704, 706, and 708 include optical filters 712 that transmit a specific wavelength of light while filtering out other wavelengths, such as interference filters. Each detector module includes a detector 716 for detecting light that is transmitted through the filters 712 (e.g., a photodiode). In the case of the broadband detector module 710, a filter is not used. Each detector module also includes a set of optics 714 for directing light from the set of optical fibers 704 through the filters 712 and onto the detectors 716.

The detection system 700 can have a number of different detector module configurations. For example, in the embodiment shown in FIG. 7, the detector system includes five modules. Detector module 702 is set to a wavelength of 1070 nm, which is representative of a hydrocarbon color channel. Detector module 704 is set to 1445 nm, which is a water peak channel. Detector module 706 is set to 1600 nm, which is a hydrocarbon baseline channel, and detector module 708 is set to 1725 nm, which is a hydrocarbon peak channel. Detector module 710 has a wide measurement dynamic range to reliably detect phase transitions (e.g., 700 nm to 1600 nm). In other embodiments, the detector system uses two detector modules (e.g., one module is set to 1070 nm and the other module is set to 1600 nm). Furthermore, for certain applications, the detector system uses a single detector module (e.g., a single broadband module).

Referring back to FIG. 6, in various embodiments, the light from the source 606 is transmitted within the fluid sample along a short path length 625. The path length is a distance within a detection chamber between optical elements, such as ball lenses or windows. In FIG. 6, the path length is represented by reference symbol d and is the distance between ball lenses 614 and 616. In some embodiments, this path length is a short path length of less than 2 mm. In other embodiments, the path length is less than 1 mm. This short path length facilitates measurement of the asphaltene onset pressure.

Longer path lengths within formation fluids produce greater scattering and absorption of light. This is particularly true for asphaltenes which produce clusters and sediments that scatter light. To overcome this problem, the inventors took an approach that is contrary to what they understood to be conventional wisdom. They shortened the path length to less than 2 mm. The short path length produces a reliable light signal, while permitting use of a more energy efficient light source, in contrast to the intense light source used in laboratory techniques. The more energy efficient light source is particularly beneficial for wellbore applications, which have low power constraints and high temperature operating conditions. Those in the art recognize significant disincentives associated with using short path lengths within flow lines that contain formation fluids. Use of short path lengths risks clogging the flow line, particularly when asphaltenes flocculate within the flow line. Nevertheless, the inventors recognized that this is not a significant risk because repressurization of the formation fluid can be used to re-dissolve flocculated asphaltenes and then flush away the formation fluid, even in such small flow lines.

The system 600 also includes a pressure unit 626 for changing the pressure within the fluid sample and a pressure sensor 628 that monitors the pressure of the fluid sample. The pressure unit 626 is not drawn to scale in FIG. 6. In one specific embodiment, the pressure unit 626 is a piston that is in communication with the detection chamber 604 and that expands the volume of the fluid sample to decrease the pressure of the sample within the detection chamber. A pressure sensor 628 is used to monitor the actual pressure within the fluid sample. The pressure sensor 628 can be a strain gauge or a resonating pressure gauge.

To more effectively control pressure within the detection chamber 604, the system 600 may include valves 622 and 624 that remain closed when the pressure unit 626 is varying the pressure of the fluid sample. In one embodiment, the valves are needle valves that use a metal seal to isolate the sample. For fluids that contains sand and particulates, other valves can be used, such as valves that use rubber seals. The valves 622 and 624 can couple the detection chamber 604 to (i) a sample bottle within the wellbore tool, (ii) a flow line within the wellbore tool, (iii) a waste disposal system within the wellbore tool, or (iv) any combination of such elements. For example, in one embodiment, the valves 622 and 624 are opened to introduce a new fluid sample into the detection chamber 604 from a flow line and an old sample is flushed out into a waste disposal system.

In illustrative embodiments, the volume of the detection chamber 604 (between the valves 622 and 624) is less than 1 mL. This small volume size provides for use of small sample volumes, which, in turn, permits measurements on a number of different sample volumes without significantly depleting available fluid. Small sample volumes are particularly beneficial in wellbore applications where the volume of formation fluid drawn into the wellbore tool is limited.

The system 600 may also include a temperature detector 629, such as a resistive temperature detector (RTD), that is in thermal communication with the fluid sample and measures the temperature of the fluid sample. In one specific embodiment, the temperature detector 629 is in thermal contact with the housing 602 and can measure the temperature of the fluid sample within the detection chamber 604.

The system 600 also includes a controller 630 for controlling the system 600 and processing signals that are received from various components within the system. The controller 630 receives one or more transmitted light signals that are representative of the intensity of the transmitted light from the light detector system 608 and one or more detector modules. The controller 630 may use the transmitted light signal from two or more wavelength-specific detector modules to determine a wavelength dependent signal. A process for determining a wavelength dependent signal is further described below. The controller 630 can also be in electronic communication with the pressure unit 626 and the pressure sensor 628. The controller 630 modifies the pressure within the detection chamber 604 by controlling the pressure unit 626 and also monitors the actual pressure within the sample by interpreting an output pressure signal from the pressure sensor 628. In some embodiments, the controller samples the output pressure signal at a sampling rate of between 10 Hz and 60 Hz. The controller 630 may also maintain timing (e.g., synchronization) between the transmitted light signal from the light detector 608 and the output pressure signal within the sample so that corresponding portions between the transmitted light signal and the output pressure signal can be identified. In an asynchronous embodiment, the controller 630 may sample the transmitted light signal at a high sampling rate, such as 100 Hz. In some embodiments, the controller 630 samples the transmitted light signal at a frequency of at least 25 Hz.

Illustrative embodiments of the system 600 are not limited to the embodiments shown in FIGS. 6 and 7. For example, in some embodiments, a flat planar window can serve to prevent outflow of the fluid and a ball lens can be positioned behind the planar window. In another illustrative embodiment, a light emitting diode (LED) is used in place of the tungsten halogen lamp.

Further details of devices and systems for determining bubble point pressure are provided in U.S. patent application Ser. No. 13/403,989, filed on Feb. 24, 2012, and U.S. patent application Ser. No. 13/800,896, filed on Mar. 13, 2013. Both of these applications are incorporated by reference herein in their entireties.

Figure 8:
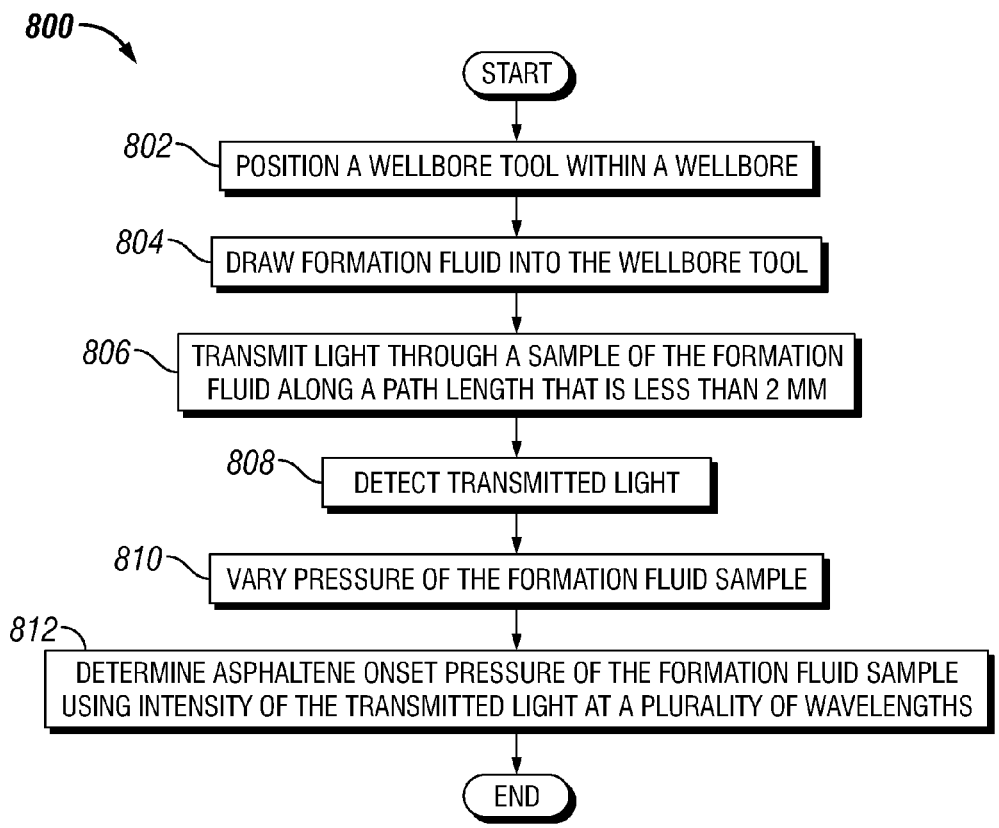
FIG. 8 shows a method for determining asphaltene onset pressure of a fluid sample in accordance with one embodiment of the present disclosure.

FIG. 8 shows a method 800 for determining asphaltene onset pressure of a formation fluid. The method can be implemented by the systems described above (e.g., system 600 and light detection system 700).

At process 802 of the method, a wellbore tool is positioned within a wellbore that traverses a formation. The wellbore tool may be a wireline tool, such as the one shown in FIG. 5, or some other tool, such as a logging-while-drilling (LWD) tool.

At process 804, the formation fluid is drawn into the wellbore tool. In a formation sampling application, the formation fluid can be drawn into the wellbore tool using a probe that extends into the formation and withdraws the formation fluid from the formation. In a production logging application, the formation fluid within the wellbore may enter the wellbore tool through a port within the housing of the tool.

At process 806, light is transmitted through a sample of the formation fluid and, at process 808, the transmitted light is detected. These processes can be implemented using the system described in FIG. 6. The light is transmitted through the sample along a path length that is less than 2 mm. The short path length produces a reliable light signal. Also, the light is detected by a detector system that can detect intensity of light at a number of different wavelengths.

At process 810, the pressure of the formation fluid sample is varied. For example, in one embodiment, the pressure of the formation fluid sample is decreased from 5000 psi to 2500 psi. In illustrative embodiments, the pressure is lowered at a rate between 1 to 200 psi per second. This decrease in pressure may be performed incrementally, in steps, and/or continuously. The decrease in pressure also occurs while the system is transmitting and detecting light. Process 810 can be performed by the pressure unit and monitored by the pressure sensor, as described above.

As the pressure unit decreases the pressure within the fluid sample, the fluid sample will eventually reach the asphaltene onset pressure. At the asphaltene onset pressure (and below the asphaltene onset pressure), the intensity of the transmitted light will decrease due to scattering and absorption caused by the flocculated asphaltenes. The amount of scattering and absorption caused by the flocculated asphaltenes will depend on the wavelength of the light. In contrast, at the bubble point pressure (and below the bubble point pressure), bubbles produced within the fluid sample scatter light independent of wavelength.

At process 812, by using intensity of the transmitted light at a number of different wavelengths, the method can determine the asphaltene onset pressure of the fluid sample, while distinguishing the asphaltene onset pressure from phase transitions, such as bubble point. In particular, the asphaltene onset pressure can be determined by (i) comparing an intensity of transmitted light at a first wavelength (e.g., 1070 nm) to an intensity of transmitted light at a second wavelength (e.g., 1600 nm) and identifying a relative change between the two intensities in proportion to baseline intensity for each wavelength. The intensity of the transmitted light at the first wavelength and the intensity of the transmitted light at the second wavelength can be compared by, for example, subtracting one from the other and/or dividing one from the other (e.g., a ratio). The baseline intensity for each wavelength can be determined at any point before the asphaltene onset pressure is reached (e.g., before the pressure variation in process 810 is initiated). The wavelengths should be selected so that the relative change can be reliably identified. Generally, a large difference in the wavelengths produces a large relative change. In one embodiment, the difference between the first wavelength and the second wavelength is at least 100 nm. In another embodiment, the difference between the first wavelength and the second wavelength is at least 1000 nm.

A wavelength dependent signal can be used to identify the asphaltene onset pressure. The wavelength dependent signal can be determined using (i) the intensity of the transmitted light at the first wavelength and (ii) the intensity of the transmitted light at the second wavelength. The controller described above can be used to maintain timing (e.g., synchronization) between transmitted light signals representative of two or more wavelengths. The controller can be used generate the wavelength dependent signal using transmitted light signals representative of two or more wavelengths. In one specific embodiment, the relative light signal can be determined by subtracting (i) a baseline difference value for the two intensities at two different wavelengths (ii) from a difference value for the two intensities at time (t), as shown in the following relationship:

$$\text{Wavelength dependent signal}(t) = [I(\lambda_1, t) - I(\lambda_2, t)] - [I(\lambda_1, t_0) - I(\lambda_2, t_0)] \quad \text{Eq. 1}$$

where $I(\lambda_1, t)$ is the intensity of the transmitted light at the first wavelength at time t, $I(\lambda_2, t)$ is the intensity of the transmitted light at the second wavelength at time t, $I(\lambda_1, t_0)$ is a baseline intensity of transmitted light at the first wavelength, and $I(\lambda_2, t_0)$ is a baseline intensity of transmitted light at the second wavelength. In Equation 1, the intensity of the transmitted light can be represented as an optical density, which can be determined according to the following relationship:

$$\text{Optical Density} = \log_{10} \frac{I_{out}}{I_{in}} \quad \text{Eq. 2}$$

where $I_{in}$ corresponds to the intensity provided by the light source and $I_{out}$ corresponds to the light detected at the detector (e.g., after a portion of the light is absorbed by the sample).

Equation 1 is one example of a relationship that can be used to determine a wavelength dependent signal. Other relationships can also be used to determine the wave length dependent signal. For example, in one embodiment, the wavelength dependent signal is determined by dividing a difference value for the two intensities at different wavelengths by a baseline difference value for the two intensities at time (t), as shown in the following relationship:

$$\text{Wavelength dependent signal } (t) = \frac{I(\lambda_1, t) - I(\lambda_2, t)}{I(\lambda_1, t_0) - I(\lambda_2, t_0)} \quad \text{Eq. 3}$$

In another embodiment, wavelength dependent signal is determined by subtracting a baseline ratio for the two intensities at different wavelengths from a ratio for the two intensities at time (t), as shown in the following relationship:

$$\text{Wavelength dependent signal } (t) = \frac{I(\lambda_1, t)}{I(\lambda_2, t)} - \frac{I(\lambda_1, t_0)}{I(\lambda_2, t_0)} \quad \text{Eq. 4}$$

The asphaltene onset pressure of the fluid sample can be determined using the wavelength dependent signal. As explained above, at the asphaltene onset pressure, asphaltenes will flocculate and this behavior will result in a change within the wavelength dependent signal. The asphaltene onset pressure of the fluid sample is determined by identifying a change within the wavelength dependent signal as the pressure of the fluid sample is decreased. In a particular embodiment, the asphaltene onset pressure of the fluid sample is determined by identifying an increase within the wavelength dependent signal as the pressure of the fluid sample is decreased.

Figure 9A:
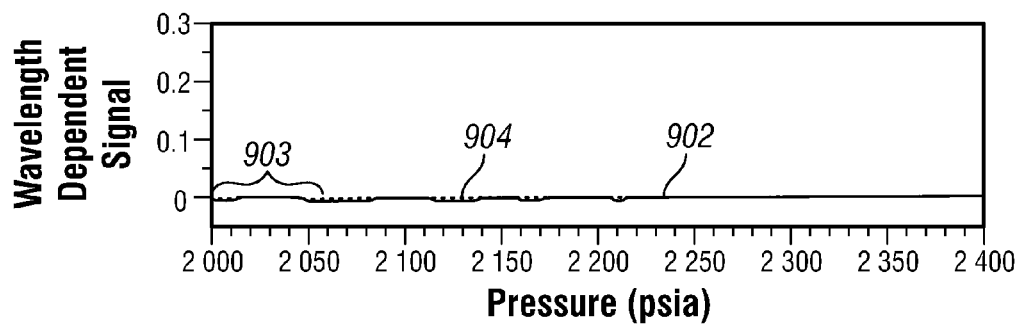
FIG. 9A shows plots of wavelength dependent signals versus pressure for a fluid with a bubble point, but with no asphaltene onset pressure, in accordance with one embodiment of the present disclosure.

FIG. 9A shows plots of wavelength dependent signals versus pressure for a fluid with a bubble point, but with no asphaltene onset pressure. The wavelength dependent signal was determined according to Equation 1 using wavelengths of 1070 nm and 1600 nm (plot 902) and wavelengths of 1445 nm and 1600 nm (plot 904).

Figure 9B:
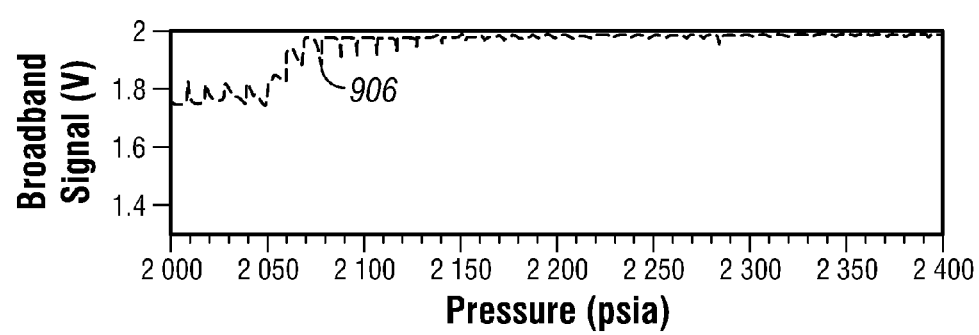
FIG. 9B shows a plot of broadband signal versus pressure for a fluid with a bubble point, but with no asphaltene onset pressure.

FIG. 9B shows a plot of a broadband signal (plot 906) versus pressure for the fluid with a bubble point, but with no asphaltene onset pressure. The broadband signal was generated by a broadband detector module, as described above in FIG. 7.

Figure 9C:
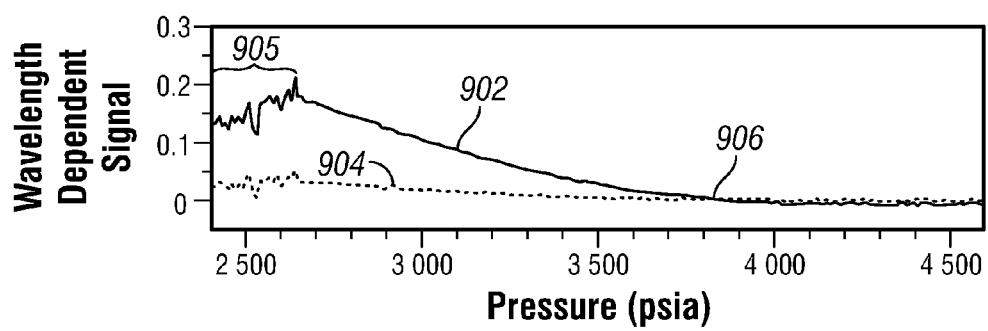
FIG. 9C shows plots of wavelength dependent signals versus pressure for a fluid with both a bubble point and an asphaltene onset pressure in accordance with one embodiment of the present disclosure.

FIG. 9C shows plots of wavelength dependent signals versus pressure for a fluid with both a bubble point and an asphaltene onset pressure.

Figure 9D:
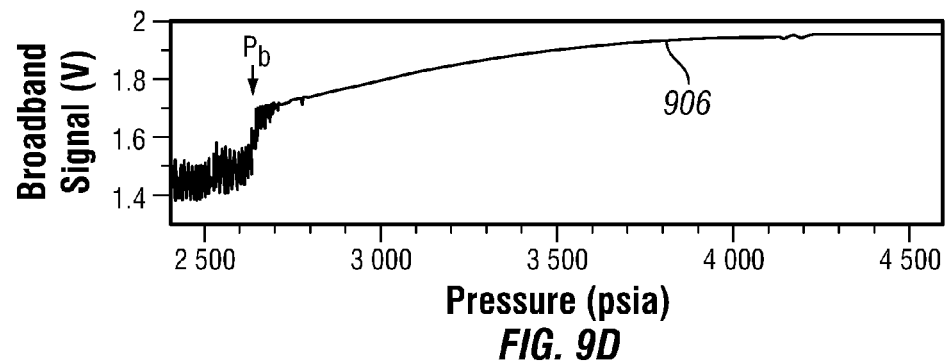
FIG. 9D shows a plot of broadband signal versus pressure for the fluid with both a bubble point and an asphaltene onset pressure.

FIG. 9D shows a plot of a broadband signal (plot 906) versus pressure for the fluid with both a bubble point and an asphaltene onset pressure.

As shown in FIGS. 9A and 9C, the wavelength dependent signal remains constant while the pressure within the sample is decreased. At point 906, in FIG. 9C, however, both wavelength dependent signals 902 and 904 suddenly increase below 4000 psi. The sudden increase is greater in plot 902 because of the large difference in wavelengths used to generate the signal. This sudden increase indicates that the asphaltenes have started flocculating and the pressure at which this increase happens is the asphaltene onset pressure. In this example, the asphaltene onset pressure is approximately 4000 psi. Since there is no asphaltene onset pressure in FIG. 9A, both wavelength dependent signals 902 and 904 remain unchanged as the pressure is reduced in that FIG. 903). The asphaltene onset pressure can be confirmed by identifying a change within the broadband signal that corresponds in pressure to the change in the wavelength dependent signal. FIG. 9D shows a corresponding decrease in the broadband signal at 4000 psi.

As explained above, the wavelength dependent signal remains unaffected by formation of bubbles within the fluid sample. FIG. 9B shows a decrease in broadband signal at approximately 2070 psi and FIG. 9D shows a decrease in broadband signal at approximately 2650 psi. These decreases are associated with bubble points. As shown in FIG. 9A, both wavelength dependent signals 902 and 904 remain unchanged during the bubble point (903). In FIG. 9C, the wavelength dependent signals 902 and 904 have some noise below the bubble point, but both signals stop increasing once bubbles appear (905). In this manner, the bubble point and asphaltene onset pressure can be identified and distinguished.

Figure 10:
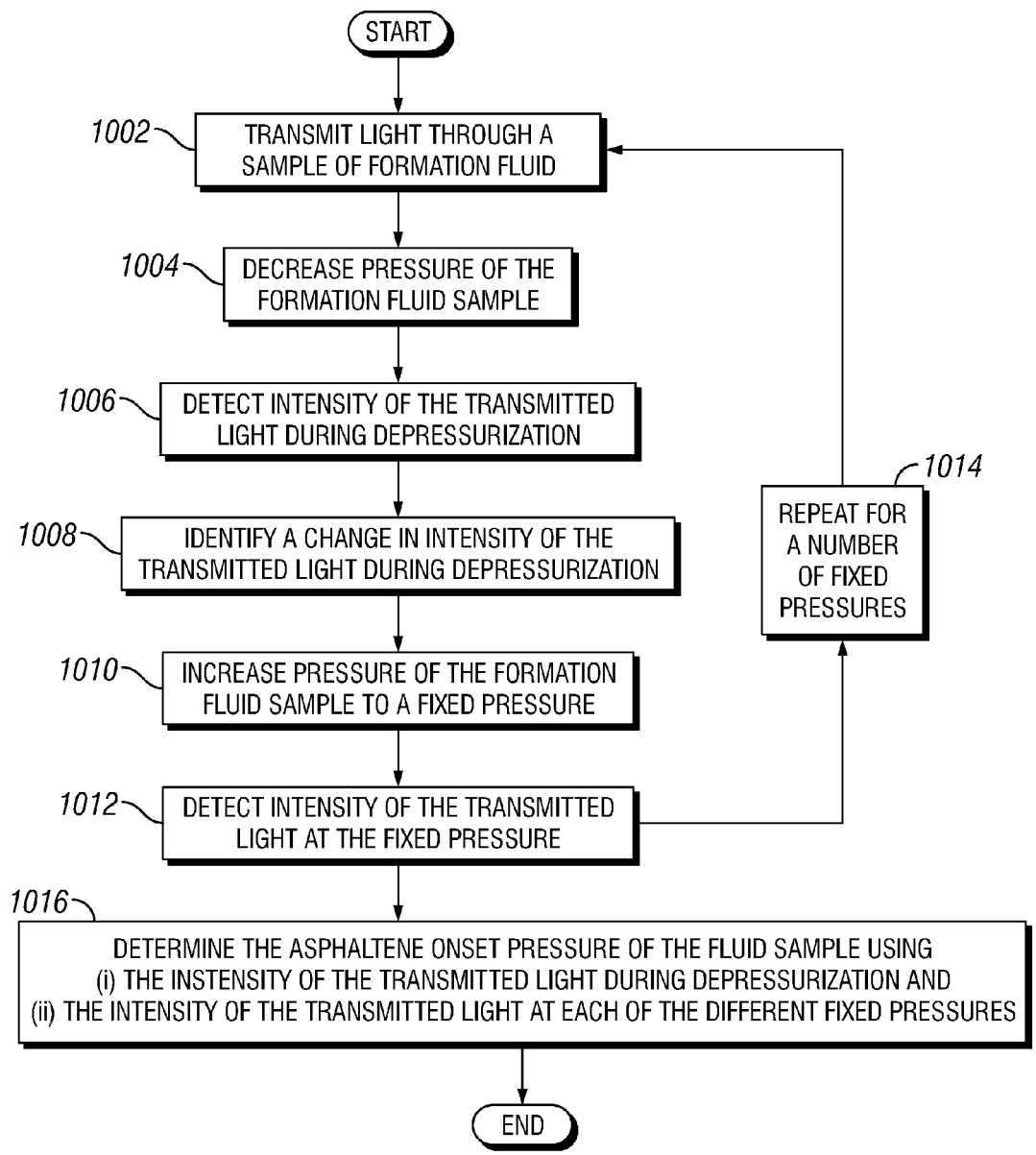
FIG. 10 shows a method for determining asphaltene onset pressure of a fluid sample in accordance with another embodiment of the present disclosure.

FIG. 10 shows another method 1000 for determining asphaltene onset pressure of a formation fluid. The method can be implemented by the systems described above (e.g., system 600). Prior to the first process 1002, a sample of formation fluid enters the detection chamber of the system. In one embodiment, the formation fluid sample is extracted from a flow line of a wellbore tool (e.g., a wireline or logging-while-drilling (LWD) tool), which, in turn, was extracted from a location-of-interest within the formation.

The method thus begins at process 1002, which transmits light through the formation fluid sample using a light source. In some embodiments, the light is transmitted through the sample along a path length that is less than 2 mm. The short path length produces a reliable light signal.

At process 1004, the pressure of the formation fluid sample is varied. For example, in one embodiment, the pressure of the formation fluid sample is decreased until asphaltene flocculation occurs. In one example, the pressure is decreased from an initial pressure of 10,000 psi to a pressure of 6,000 psi. This decrease in pressure may be performed incrementally, in steps, and/or continuously. The behavior of asphaltene flocculation depends on the rate of depressurization. Rapid depressurization may overshoot the actual asphaltene onset pressure. Accordingly, in various embodiments, the pressure is decreased so that a more accurate measure of asphaltene onset pressure is determined. In illustrative embodiments, the rate of depressurization is between 10 to 100 psi/second.

At process 1006, intensity of the transmitted light during depressurization is detected. In one embodiment, this process is performed using a broadband detection module and a broadband signal, as described above. In another embodiment, this process is performed using the detection system described in FIG. 7, which detects the intensity of light at a number of different wavelengths and outputs a wavelength dependent signal.

At process 1008, a change in intensity of the transmitted light during depressurization is identified. This change represents asphaltene flocculation. Generally, as the pressure is reduced, the intensity of the transmitted light signal will increase. A reversal of this trend may indicate asphaltene flocculation. Any one of the broadband signal, the wavelength dependent signal, or both can be used to identify the asphaltene flocculation. As described above, the wavelength dependent signal beneficially identifies asphaltene flocculation, while distinguishing asphaltene flocculation, from phase changes, such as bubble point.

At process 1010, once asphaltene flocculation is observed, the pressure of the formation fluid sample is increased to a fixed pressure. Although the depressurization rate is slow, once asphaltene flocculation is observed, the pressure of the formation fluid sample is rapidly increased to reduce time at lower pressures (e.g., 100 psi per second). This rapid increase in pressure increases the reversibility of the flocculation process. Also, at the lower pressures, the sample may produce undesirable sedimentation. Sedimentation is the settling of flocculated asphaltenes within the formation fluid sample. Thus, in various embodiments, the rapid increase in pressure helps prevent clogging in system that use short light path lengths.

At process 1012, the intensity of the transmitted light at the fixed pressure is detected. The intensity of the transmitted light is used in process 1016 (described below) to determine asphaltene onset pressure. Initially, at the fixed pressure, the intensity of the transmitted light will increase as a function of time as some of the asphaltenes will dissolve. An equilibrated intensity of the transmitted light signal (e.g., wavelength dependent signal or broadband signal) is used to determine the asphaltene onset pressure in process 1016. In some embodiments, the equilibrated light signal is determined by allowing the intensity of the light signal to equilibrate (e.g., reach a steady state value) and then identifying the equilibrated signal. The time necessary for the signal to equilibrate will depend on the sample. In some cases, the signal may take many minutes or hours to equilibrate. To more efficiently determine the equilibrated signal, the equilibrated signal can be extrapolated from the signal that has already been recorded at the fixed pressure. In this manner, the equilibrated signal can be determined before the signal reaches a steady state value. The equilibrated signal can be extrapolated by applying a fit (e.g., an exponential fit) to the signal already recorded.

In some cases, at the fixed pressure, the transmitted light signal will slowly increase and then suddenly start to decrease. The sudden decrease indicates sedimentation within the fluid. If sedimentation is detected in this manner, then the equilibrated signal should be extrapolated from recorded signal that occurs before the sedimentation.

Figure 11:
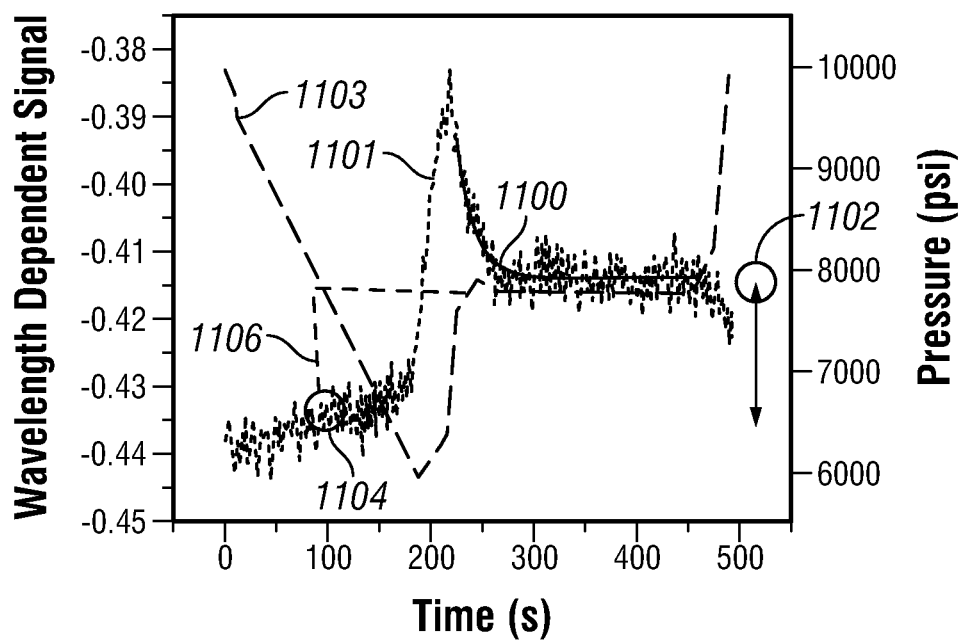
FIG. 11 shows a plot of a wavelength dependent signal and pressure versus time for a crude oil sample in accordance with one embodiment of the present disclosure.

FIG. 11 shows a plot of a wavelength dependent signal (1101) and pressure (1103) versus time for a crude oil sample with an asphaltene onset pressure. Processes 1002 to 1012 were applied to the sample. The pressure of the oil sample was slowly reduced from 10,000 psi. At 6,000 psi, a change in the wavelength dependent signal is identified. The oil sample is then pressurized to a fixed pressure of 7,750 psi. The sample is maintained at this pressure for over 200 seconds so that the wavelength dependent signal can move towards a steady state. An exponential fit 1100 is applied to the signal data to extrapolate an equilibrated signal. At about 450 seconds, the wavelength dependent signal decreases. This decrease may indicate sedimentation. Accordingly, the portion of the wavelength dependent signal after 450 seconds is not used to determine the equilibrated signal.

Referring back to FIG. 10, at process 1014, processes 1002 to 1012 are repeated a number of times for different fixed pressures (e.g., 2, 3, 5, 10, or 20). In one embodiment, a lowest desirable fixed pressure can be used initially and the fixed pressure of each subsequent repetition is incrementally increased by a pressure value (e.g., 100 psi, 250 psi, 500 psi, or 1000 psi). The number of fixed pressures and size of each increment will depend on available time and desired accuracy. In one embodiment, the repetitions are performed until full recovery of the transmitted light signal is obtained. In another embodiment, the number of repetitions may depend on the outcome of process 1016 below. For example, the processes are repeated until an accurate asphaltene onset pressure for the fluid sample is determined in process 1016 below.

In some embodiments, processes 1002 to 1012 are repeated for different formation fluid samples. After process 1012, the formation fluid sample is flushed from the detection chamber and a new formation fluid sample enters the detection chamber. Processes 1002 to 1012 are performed on the new formation fluid sample. Using a new formation fluid sample for each repetition is beneficial because the depressurization process 1004 may produce irreversible sedimentation and decrease the amount of signal recovery observable during each repetition. As explained above, in illustrative embodiments, the volume of the detection chamber is small (e.g., less than 1 mL) and this small volume provides for many repetitions using different samples without significantly depleting available fluid.

In other embodiments, at process 1014, processes 1010 to 1012 are repeated for the same formation fluid sample. The fixed pressure is incrementally increased from a lowest desirable pressure and the intensity of transmitted light is recorded at each fixed pressure (e.g., extrapolated).

At process 1016, the asphaltene onset pressure of the fluid sample is determined using (i) the intensity of the transmitted light during each depressurization (e.g., intensity of wavelength dependent signal in process 1006) and (ii) the intensity of transmitted light at each of the different fixed pressures (e.g., intensity of equilibrated wavelength dependent signal in process 1012). The asphaltene onset pressure is determined by subtracting (i) the equilibrated intensity of the transmitted light at each fixed pressure (during each process 1012) from (ii) the intensity of the transmitted light during depressurization corresponding to each fixed pressure (during each respective process 1006) to determine difference values at each of the different fixed pressures. For example, in FIG. 11, the difference value is 0.025 for a fixed pressure of 7,750 psi. The difference value is determined by subtracting an extrapolated intensity of 0.412 at the fixed pressure (1102) from an intensity of 0.437 (1104), which is the intensity of the wavelength dependent signal at 7,750 psi during the depressurization process 1006. Dashed line 1106 shows how the intensity of the transmitted light during depressurization (that corresponds to the fixed pressure) is determined.

The asphaltene onset pressure can be determined by identifying a difference value that is (i) a value of zero, (ii) a steady state value, or (iii) both. The fixed pressure that corresponds to the identified difference value is the asphaltene onset pressure. In formation fluid samples where the asphaltene flocculation is completely reversible, a difference value of zero will be representative of the asphaltene onset pressure. In formation fluid samples that are not completely reversible, a difference value that corresponds to a first steady state value (with increasing pressure) will be representative of the asphaltene onset pressure.

Figure 12:
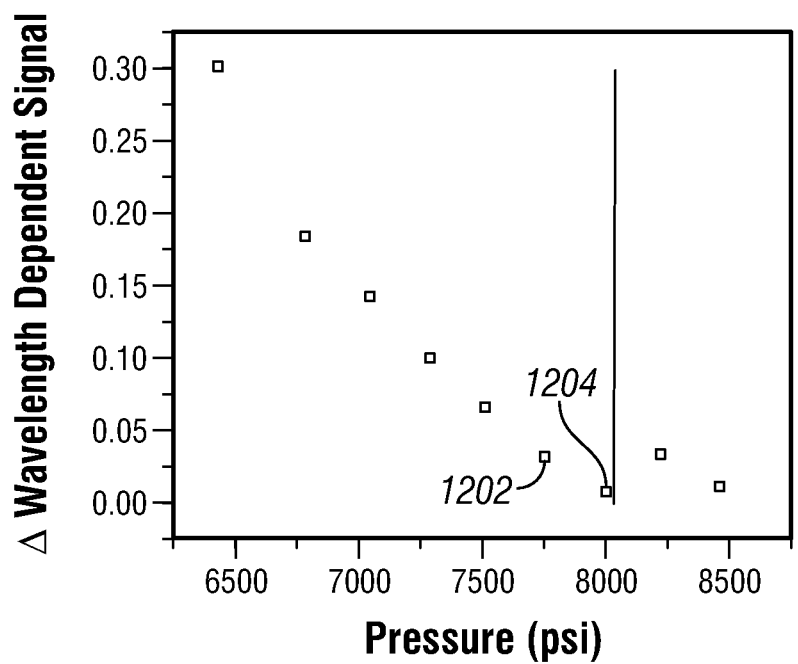
FIG. 12 shows a plot of difference values for wavelength dependent signals versus fixed pressures for the crude oil sample in accordance with one embodiment of the present disclosure.

FIG. 12 shows a plot of difference values for wavelength dependent signals versus fixed pressures for the crude oil sample. Processes 1002 to 1014 were applied to the sample. Processes 1002 to 1012 were initially applied for a fixed pressure of 6,500 psi. Processes 1002 to 1012 were repeated 8 times and the fixed pressures were incremented by 250 psi. Point 1202 corresponds to the difference value determined from FIG. 11. The plot reaches a steady state value at point 1204, which corresponds to a fixed pressure of 8,000 psi. Thus, the asphaltene onset pressure of the crude oil sample is 8,000 psi. This value compares well with an asphaltene onset pressure of 8,030 psi, which was determined using a time intensive laboratory technique.

Figure 13:
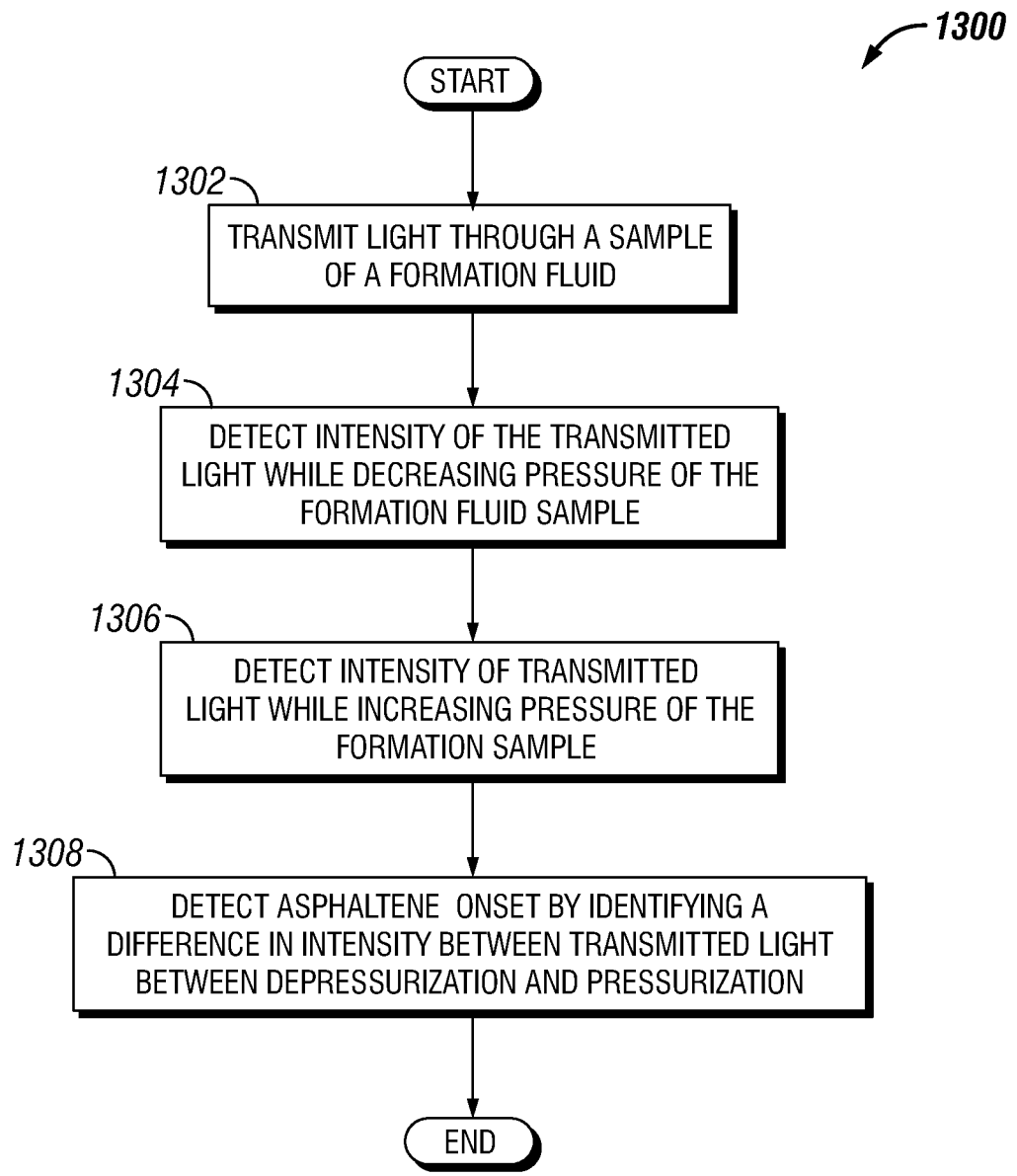
FIG. 13 shows a method for detecting asphaltene onset of a formation fluid in accordance with one embodiment of the present disclosure.

FIG. 13 shows a method 1300 for detecting asphaltene onset of a formation fluid. The method 1300 can be used to confirm the presence of an asphaltene onset before another method is used to determine a specific value for asphaltene onset pressure, such as the method 1000 shown in FIG. 10. The method 1300 can also provide upper and lower bounds for the asphaltene onset pressure. Thus, in illustrative embodiments, the method 1300 prevents time consuming analysis of formation fluid when no asphaltene onset occurs and informs identification of the asphaltene onset pressure at a particular range of pressures when an asphaltene onset does occur.

The method 1300 can be performed by the detection system 600 shown in FIG. 6, but can also be implemented by other systems. The method begins at process 1302, where light is transmitted through a sample of formation fluid using a light source. At process 1304, the intensity of the transmitted light is detected while the pressure of the formation fluid sample is decreased to a predetermined pressure. In various embodiments, the depressurization begins at an initial pressure that corresponds to formation or wellbore pressure. The pressure is then decreased to a lower pressure value.

There are a number of different ways to select the lower pressure value. For example, the lower pressure value can be selected by identifying a decrease within the intensity of the transmitted light as the pressure of the sample is decreased. In another embodiment, the lower pressure value can be a predetermined pressure value that is selected so that the value is greater than the bubble point pressure of the formation fluid sample. Lowering the pressure below the bubble point pressure will cause bubbles to nucleate and their presence will complicate identification of the asphaltene onset pressure. The bubble point pressure can be determined or estimated from other known methods, such as the method described in U.S. patent application Ser. No. 13/800,896, filed on Mar. 13, 2013, which is hereby incorporated by reference in its entirety.

At process 1306, the intensity of the transmitted light is decreased while increasing pressure of the formation fluid sample. The pressurization process begins at the lower pressure value and in some embodiments, continues to the initial pressure.

The intensity of the light signal is recorded during the depressurization process 1304 and the pressurization process 1306. These processes can be performed using a broadband signal or a wavelength dependent signal, as described above.

As explained above, the behavior of asphaltene flocculation depends on a rate of depressurization. The dissolution of asphaltenes will also depend on a rate of pressurization. Thus, the depressurization process 1304 and the pressurization process 1306 are performed slowly so that a more accurate measure of asphaltene onset pressure is determined. In illustrative embodiments, the rate of depressurization and pressurization is less than 100 psi/second (e.g., less than 50 psi, 20 psi, or 10 psi).

At process 1308, asphaltene onset is detected by identifying a difference in intensity between transmitted light during the depressurization process 1302 and transmitted light during the pressurization process 1304. If the formation fluid contains asphaltenes and the asphaltenes flocculate during the depressurization process 1302, then there will be hysteresis between transmitted light during the depressurization process 1302 and transmitted light during the pressurization process 1304. The transmitted light during the pressurization process 1304 will be lower than the transmitted light during the depressurization process 1302. The hysteresis is caused because the flocculated asphaltenes do not quickly dissolve into the formation fluid. If the formation fluid contains no asphaltenes and asphaltenes do not flocculate during the depressurization process 1302, then the transmitted light during the depressurization process 1302 will approximately correspond to transmitted light during the pressurization process 1304.

Hysteresis may also be caused by bubbles produced when the bubble point is reached. Thus, in various embodiments, the bubble point is excluded from affecting the measurement (i) by selecting the lower pressure value to be above the bubble point pressure or (ii) by distinguishing between hysteresis produced by asphaltenes and bubbles. Hysteresis caused by asphaltenes shows a much slower recovery than hysteresis caused by bubbles.

The method 1300 can be used to determine upper and lower bounds for the asphaltene onset pressure. For example, the lower pressure value can be used as the lower bound for the asphaltene onset pressure. An upper bound can be determined by identifying a pressure at which the intensity of transmitted light during the depressurization process 1302 and the intensity of transmitted light during the pressurization process 1304 intersect (e.g., the lowest pressure where the intensity values are equal).

Figure 14:
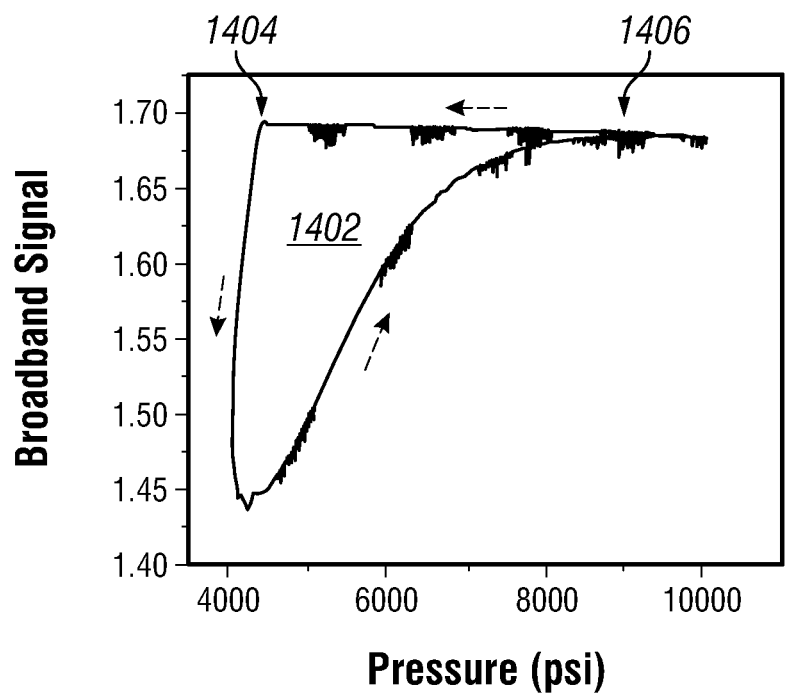
FIG. 14 shows a plot of broadband signal versus pressure for a crude oil sample with an asphaltene onset pressure in accordance with one embodiment of the present disclosure.

FIG. 14 shows a plot of broadband signal versus pressure for a crude oil sample with an asphaltene onset pressure. Processes 1302 to 1318 were applied to the sample. The pressure of the oil sample was slowly reduced from 10,000 psi to 4,000 psi. Then, the pressure of the oil sample was increased from 4,000 psi to 10,000 psi. The plot shows that asphaltene flocculation occurred within the oil sample because a large difference in transmitted light intensity between depressurization and pressurization in present within the plot. The plot forms a loop 1402, which shows hysteresis and is an indicator that asphaltene flocculation occurred. The plot can be used to determine the upper and lower bounds for the asphaltene onset pressure. In this case, the lower bound of the asphaltene onset pressure corresponds to 4,400 psi, where the intensity of the transmitted light decreases during the depressurization process 1404. The upper bound of the asphaltene onset pressure corresponds to 9,000 psi, where the intensity of transmitted light during the depressurization process and the intensity of transmitted light during the pressurization process intersect 1406.

Figure 15:
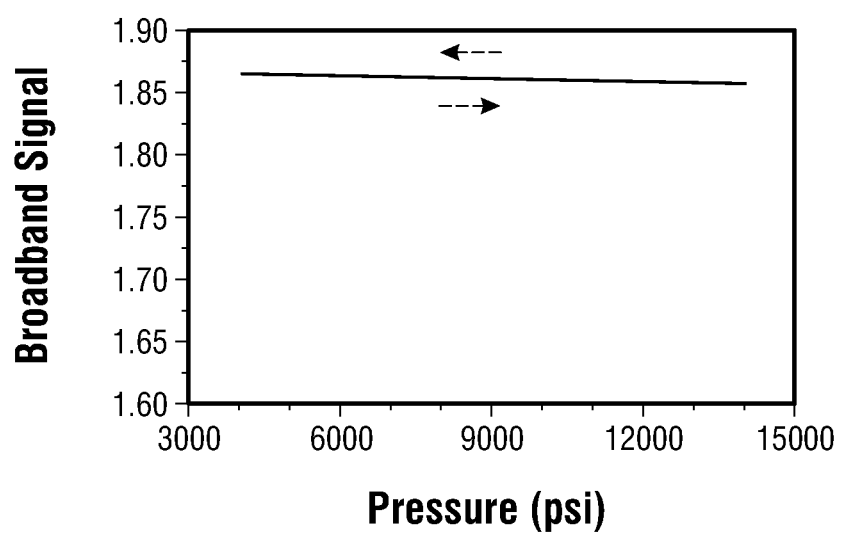
FIG. 15 shows a plot of broadband signal versus pressure for a crude oil sample without an asphaltene onset pressure in accordance with one embodiment of the present disclosure.

FIG. 15 shows a plot of broadband signal versus pressure for a crude oil sample without an asphaltene onset pressure. Processes 1302 to 1318 were applied to the sample. The pressure of the oil sample was slowly reduced from 14,000 psi to 4,000 psi. Then, the pressure of the oil sample was increased from 4,000 psi to 14,000 psi. The plot shows that the asphaltene flocculation did not occur because the transmitted light during the depressurization process corresponds to transmitted light during the pressurization process. Hysteresis does not appear in the plot. In both FIGS. 14 and 15, pressure was not dropped below the bubble point pressure of the samples.

The asphaltene onset pressure is determined for a particular temperature. In many cases, the asphaltene onset pressure is a function of both the pressure of the fluid sample and the temperature of the fluid sample. The temperature at which the asphaltene onset pressure occurs can be measured by a temperature detector, such as the temperature detector 629 shown in FIG. 6.

Some of the processes described herein, such as (i) determining asphaltene onset pressure of a fluid sample, (ii) receiving a transmitted light signal representative of an intensity of transmitted light at one or more wavelengths, (iii) determining a wavelength dependent signal, (iv) identifying a change within a broadband or wavelength dependent signal, (v) subtracting light intensities, (vi) interpreting an output pressure signal from a pressure sensor, (vii) controlling a pressure unit, (viii) extrapolating an equilibrated intensity of transmitted light at a fixed pressure, (ix) opening and closing valves, and (x) maintaining timing between transmitted light signals and an output pressure signal, can be performed by the controller.

In one specific embodiment, the controller is located within the wellbore tool along with the system for determining asphaltene onset pressure. In such an embodiment, processes (i)-(x) can be performed within the wellbore tool. In another embodiment, the controller is located at the surface as part of the surface equipment (e.g., the truck 412 in FIG. 4) and some or all of processes (i)-(x) are performed at the surface by the surface equipment. In yet another embodiment, a first controller is included within the borehole tool and a second controller is located at the surface as part of the surface equipment. In this embodiment, the processes (i)-(x) can be split between the two controllers. In yet another embodiment, some of processes (i)-(x) are performed at a location that is remote from the well site, such as an office building or a laboratory.

The term "controller" should not be construed to limit the embodiments disclosed herein to any particular device type or system. The controller may include a computer system. The computer system may also include a processor (e.g., a microprocessor, microcontroller, digital signal processor, or general purpose computer) for executing any of the methods and processes described above (e.g. processes (i)-(x)).

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. This memory may be used to store, for example, data from transmitted light signals, wavelength dependent signals, and output pressure signals.

Some of the methods and processes described above, including processes (i)-(x), as listed above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the controller may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Figure 1:
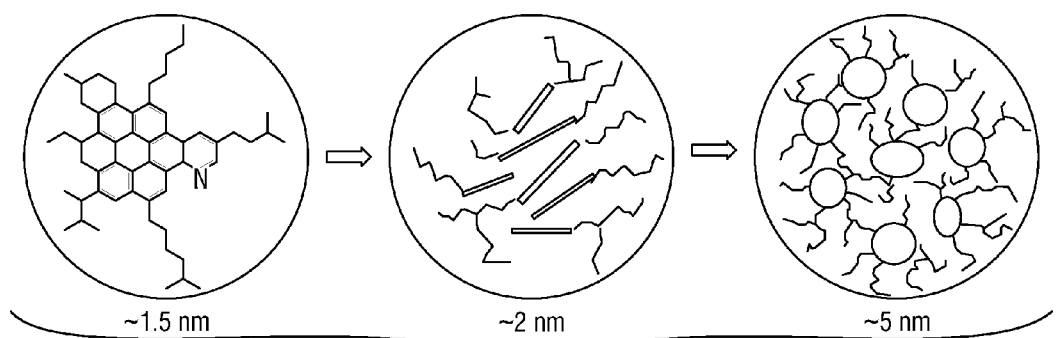
FIG. 1 shows flocculation of asphaltenes.
Figure 2:
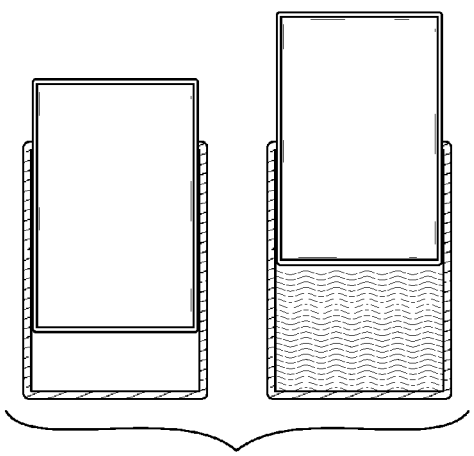
FIG. 2 shows flocculation of asphaltenes within a formation fluid sample.
Figure 3:
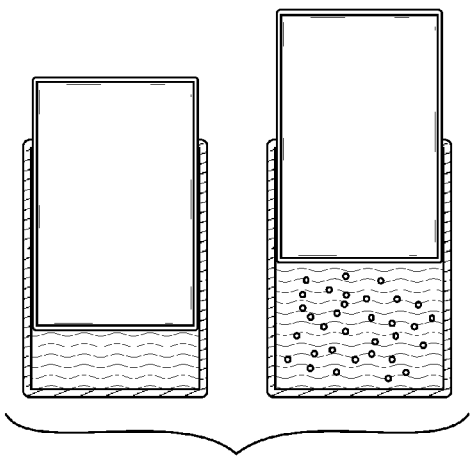
FIG. 3 shows nucleation of bubbles within a formation fluid sample.

Illustrative embodiments of the present disclosure are not limited to wireline logging operations, such as the ones shown in FIGS. 1 and 2. For example, the embodiments described herein can also be used with any suitable means of conveyance, such coiled tubing or drill pipe. Furthermore, various embodiments of the present disclosure may also be applied in logging-while-drilling (LWD) operations, sampling-while-drilling operations, measuring-while-drilling operations, production logging operations, or any other operation where sampling of formation fluid is performed.

Also, the methods and systems described herein are not limited to analyzing a set of particular fluids. Various embodiments of methods and systems described herein can be used to analyze hydrocarbons (e.g., dark oils, heavy oils, volatile oils, and black oils).

Furthermore, various embodiments of the present disclosure are not limited to oil and gas field applications. The methods and systems described herein can also be applied to, for example, petrochemical refining and chemical manufacturing.

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

What is claimed is:

1. A method for determining asphaltene onset pressure of a formation fluid, the method comprising:
   (a) transmitting light through a sample of the formation fluid;

(b) decreasing pressure of the formation fluid sample, wherein the rate of depressurization is less than 100 psi/second
(c) detecting intensity of the transmitted light during depressurization;
(d) identifying a change in intensity of the transmitted light during depressurization representative of asphaltene flocculation;
(e) increasing pressure of the formation fluid sample to a fixed pressure;
(f) detecting intensity of the transmitted light at the fixed pressure;
maintaining the pressure of the formation fluid sample at the fixed pressure until the detected intensity of the transmitted light reaches a steady state;
determining an equilibrium value by doing one of the following: allow the detected intensity of the transmitted light to reach a steady state and then identify the steady state value of the detected intensity of the transmitted light as the equilibrium value, or extrapolate the steady state value by applying a fit to the detected intensity of the transmitted light at the fixed pressure as function of time;
(g) repeating processes (a) to (f) for a plurality of different fixed pressures; and
(h) determining the asphaltene onset pressure of the fluid sample using (i) the intensity of the transmitted light from each process (c) and (ii) the intensity of the transmitted light from each process (f), wherein determining the asphaltene onset pressure of the fluid sample comprises identifying the intensity of the transmitted light during the depressurization at the fixed pressure and subtracting (i) the equilibrium value for process (f) at each different fixed pressure from (ii) the identified intensity of the transmitted light at the fixed pressure for each process (c) to determine difference values for each different fixed pressure, and wherein the asphaltene onset pressure is determined by identifying one difference value of the difference values representing at least one of (i) a value of zero and (ii) a steady state value of the difference values from a plot of the difference values vs pressure.

2. The method of claim 1, further comprising:
positioning a wellbore tool within a wellbore;
drawing the formation fluid into the wellbore tool; and
performing processes (a) to (g) within the wellbore tool.

3. The method of claim 2, wherein, in process (g), processes (a) to (f) are repeated for different formation fluid samples.

4. The method of claim 1, wherein the formation fluid sample comprises a volume equal to or less than 1 mL.

5. The method of claim 1, wherein the asphaltene onset pressure is determined by identifying a fixed pressure corresponding to the identified difference value.

6. The method of claim 1, further comprising:
determining the intensity of the transmitted light at the fixed pressure by (i) allowing the intensity of the transmitted light to equilibrate at the fixed pressure and (ii) identifying the equilibrated intensity.

7. The method of claim 1, further comprising:
determining the intensity of the transmitted light at the fixed pressure by extrapolating an equilibrated intensity of the transmitted light at the fixed pressure.

8. The method of claim 7, wherein extrapolating the equilibrated intensity of the transmitted light comprises applying an exponential fit to the intensity of the transmitted light at the fixed pressure.

9. The method of claim 1, wherein the transmitted light travels along a path length through the fluid sample that is less than 2 mm.

10. The method of claim 1, wherein processes (c) and (f) comprise detecting intensity of transmitted light at a first wavelength and a second wavelength.

11. The method of claim 10, further comprising:
determining a wavelength dependent signal using (i) the intensity of the transmitted light at a first wavelength and (ii) the intensity of the transmitted light at a second wavelength.

12. The method of claim 11, wherein process (h) comprises:
determining the asphaltene onset pressure of the formation fluid using (i) the wavelength dependent signal during each process (c) and (ii) the wavelength dependent signal during each process (f).

13. The method of claim 1, wherein identifying the intensity of the transmitted light during depressurization at the fixed pressure comprises:
analyzing pressure data of process (b) to determine a time at which the pressure equaled the fixed pressure; and
analyzing intensity data of process (d) to determine an intensity at the time at which the pressure equaled the fixed pressure.

14. A system for determining asphaltene onset pressure of a formation fluid, the system comprising:
a source for generating light that is transmitted through a sample of the formation fluid;
a detector for detecting light transmitted through the formation fluid sample;
a pressure control unit configured to vary pressure of the formation fluid sample; and
a controller configured to determine the asphaltene onset pressure of the formation fluid using (i) intensity of the transmitted light detected during each depressurization of the formation fluid sample and (ii) intensity of the transmitted light at a plurality of fixed pressures, wherein determining the asphaltene onset pressure of the formation fluid comprises:
(a) transmitting light through the sample of the formation fluid;
(b) decreasing pressure of the formation fluid sample, wherein the rate of depressurization is less than 100 psi/second
(c) detecting intensity of the transmitted light during depressurization;
(d) identifying a change in intensity of the transmitted light during depressurization representative of asphaltene flocculation;
(e) increasing pressure of the formation fluid sample to a fixed pressure;
(f) detecting intensity of the transmitted light at the fixed pressure;
maintaining the pressure of the formation fluid sample at the fixed pressure until the detected intensity of the transmitted light reaches a steady state;
determining an equilibrium value by doing one of the following: allow the detected intensity of the transmitted light to reach a steady state and then identify the steady state value of the detected intensity of the transmitted light as the equilibrium value, or extrapolate the steady state value by applying a fit to the detected intensity of the transmitted light at the fixed pressure as function of time;
(g) repeating processes (a) to (f) for a plurality of different fixed pressures; and (h) determining the asphaltene onset pressure of the fluid sample using (i) the intensity of the transmitted light from each process (c) and (ii) the intensity of the transmitted light from each process (f), wherein determining the asphaltene onset pressure of the fluid sample comprises identifying the intensity of the transmitted light during the depressurization at the fixed pressure and subtracting (i) the equilibrium value for process (f) at each different fixed pressure from (ii) the identified intensity of the transmitted light at the fixed pressure for each process (c) to determine difference values for each different fixed pressure, and wherein the asphaltene onset pressure is determined by identifying one difference value of the difference values representing at least one of (i) a value of zero and (ii) a steady state value of the difference values from a plot of the difference values vs pressure.

15. The system of claim 14, wherein the transmitted light travels along a path length through the fluid sample that is less than 2 mm.

16. The system of claim 14, wherein the system is incorporated into a wellbore tool.

17. The system of claim 16, wherein the wellbore tool comprises:
a probe for withdrawing the formation fluid sample from a formation and into the wellbore tool.

18. The system of claim 14, further comprising:
a detection chamber for at least partially containing the fluid sample, wherein the detection chamber has a volume equal to or less than 1 mL.

19. The system of claim 14, wherein identifying the intensity of the transmitted light during depressurization at the fixed pressure comprises:
analyzing pressure data during the depressurization to determine a time at which the pressure equaled the fixed pressure; and
analyzing intensity data during the depressurization to determine an intensity at the time at which the pressure equaled the fixed pressure.

* * * * *